(12) United States Patent
Gallo et al.

(10) Patent No.: US 9,703,381 B2
(45) Date of Patent: Jul. 11, 2017

(54) MULTIMODAL HAPTIC DEVICE INCLUDING A THERMAL AND TACTILE DISPLAY UNIT, SYSTEM, AND METHOD OF USING THE SAME

(71) Applicant: Ecole Polytechnique Fédérale de Lausanne (EPFL), Lausanne (CH)

(72) Inventors: Simon Gallo, Lausanne (CH); Giulio Rognini, Lausanne (CH); Tobias Lukas Bützer, Zug (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 0 days.

(21) Appl. No.: 15/016,302

(22) Filed: Feb. 5, 2016

(65) Prior Publication Data

US 2016/0238040 A1    Aug. 18, 2016

Related U.S. Application Data

(60) Provisional application No. 62/117,476, filed on Feb. 18, 2015.

(51) Int. Cl.
*G08B 21/00* (2006.01)
*G06F 3/01* (2006.01)
(Continued)

(52) U.S. Cl.
CPC ............ *G06F 3/016* (2013.01); *A61B 5/4561* (2013.01); *A61F 7/00* (2013.01); *A61H 9/0078* (2013.01);
(Continued)

(58) Field of Classification Search
CPC ............ G06F 3/00; G06F 3/016; A61H 23/04
(Continued)

(56) References Cited

U.S. PATENT DOCUMENTS 6,384,715 B1* 5/2002 Potter .................... A47C 7/467
340/407.1
6,425,764 B1* 7/2002 Lamson ................. A61M 21/00
434/236

(Continued)

FOREIGN PATENT DOCUMENTS

WO    WO 2009/061572    5/2009

OTHER PUBLICATIONS

Simon Gallo, Lucian Cucu, Nicolas Thevenaz, Ali Sengül, Hannes Bleuler, "Design and Control of a novel Thermo-tactile Multimodal Display," IEEE Haptic Symposium 2014, Houston, Texas, pp. 75-81, Feb. 23, 2014.

(Continued)

*Primary Examiner* — Mark Rushing
(74) *Attorney, Agent, or Firm* — Andre Roland S.A.; Nikolaus Schibli (57) ABSTRACT

A multimodal haptic device operating as a closed-loop system, the device including a pipeline configured to allow a closed-loop flow of a fluid medium, a manifold operatively connected to the pipeline, the manifold having a pump and a valve to control and regulate a flow of the fluid medium along the pipeline, and a display unit operatively connected to the pipeline, the display unit having a tactile display and a valve operatively connected to the tactile display for regulating an efflux of the fluid medium from the tactile display into the pipeline.

21 Claims, 6 Drawing Sheets

(51) Int. Cl.

| | | |
|---|---|---|
| *A61H 9/00* | (2006.01) | |
| *A61B 5/00* | (2006.01) | |
| *A61F 7/00* | (2006.01) | |
| *A63F 13/285* | (2014.01) | |
| *A63F 13/00* | (2014.01) | |
| *A61H 23/04* | (2006.01) | |
| *A61B 34/35* | (2016.01) | |

(52) U.S. Cl.
CPC ............ *A63F 13/00* (2013.01); *A63F 13/285* (2014.09); *A61B 34/35* (2016.02); *A61H 23/04* (2013.01); *A61H 2201/0207* (2013.01); *A61H 2201/0214* (2013.01); *A61H 2201/0228* (2013.01); *A61H 2201/0242* (2013.01); *A61H 2201/0264* (2013.01); *A61H 2201/0285* (2013.01); *A61H 2201/10* (2013.01); *A61H 2201/1635* (2013.01); *A61H 2201/1697* (2013.01); *A61H 2201/5012* (2013.01); *A61H 2201/5015* (2013.01); *A61H 2201/5043* (2013.01); *A61H 2201/5061* (2013.01); *A61H 2201/5071* (2013.01); *A61H 2201/5076* (2013.01); *A61H 2201/5082* (2013.01); *A61H 2201/5092* (2013.01); *A61H 2201/5097* (2013.01); *A61H 2205/06* (2013.01); *A61H 2205/065* (2013.01); *A61H 2230/04* (2013.01); *A61H 2230/06* (2013.01); *A61H 2230/20* (2013.01); *A61H 2230/202* (2013.01); *A61H 2230/30* (2013.01); *A61H 2230/42* (2013.01); *A61H 2230/50* (2013.01); *A61H 2230/60* (2013.01); *A61H 2230/65* (2013.01)

(58) Field of Classification Search
USPC ...................................................... 340/407.1
See application file for complete search history.

(56) References Cited

U.S. PATENT DOCUMENTS

| | | | | |
|---|---|---|---|---|
| 2003/0117371 | A1* | 6/2003 | Roberts ................... | G06F 3/014 345/156 |
| 2006/0103634 | A1* | 5/2006 | Kim ........................ | G06F 3/016 345/173 |
| 2008/0248836 | A1* | 10/2008 | Caine ..................... | G06F 1/1616 455/566 |
| 2009/0120105 | A1* | 5/2009 | Ramsay .................. | G06F 3/016 62/3.3 |
| 2014/0160044 | A1* | 6/2014 | Yairi ....................... | G06F 3/016 345/173 |

OTHER PUBLICATIONS

Armel et al., Projecting Sensations to External Objects—Evidence from Skin Conductance Response, Proc. of the Royal Society of London. Series B: Biological Sciences, vol. 270, pp. 1499-1506, 2003.
Austen, Soto-Faraco et al., Cognitive, Affective, & Behavioral Neuroscience, vol. 4, No. 2, pp. 170-181, 2004.
Avanzino et al., Shaping Motor Cortex Plasticity Through Proprioception, Cereb Cortex, vol. 24, pp. 2807-2814, 2013.
Avanzino et al., Use-Dependent Hemispheric Balance, Journal of Neuroscience, vol. 31, No. 9, pp. 3423-3428, 2011.
Bassolino et al., Functional Effect of Short-Term Immobilization, Kinematic Changes and Recovery on Reaching-to-Graps, Neuroscience, vol. 215, pp. 127-134, 2012.
Blanke, Nature Reviews Neuroscience, vol. 13, No. 8, pp. 556-571, 2012.
Botvinick et al., Rubber hands 'feel' touch that eyes see, Nature, vol. 391, No. 6669, pp. 756-756, 1998.
Dadarlat et al., A learning-based approach to artificial sensory feedback leads to optimal integration, Nature Neuroscience, vol. 18, No. 1, pp. 138-144, 2015.
Ehrsson et al., That's My Hand! Activity in Premotor Cortex Reflects Feeling of Ownership of a Limb Science, vol. 305, No. 5685, pp. 875-877, 2004.
Ehrsson, The Experimental Induction of Out-Of-Body Experiences, Science, vol. 317, No. 5841, p. 1048, 2007.
G. Nelles, Restorative Neurology and Neuroscience, vol. 22, pp. 239-244, 2004.
Hansell et al., Seeing and identifying with a virtual body decreases pain perception, European journal of pain, vol. 15, No. 8, pp. 874-879, 2011.
L.A. Connell, Sensory Impairment and recovery After Stroke, PhD thesis, University of Nottingham, United Kingdom, 2007.
Lenggenhager et al., Video Ergo Sum: Manipulating Bodily Self-Consciousness, Science, vol. 317, No. 5841, p. 1096, 2007.
Marasco et al., Robotic touch shifts perception of embodiment to a prosthesis in targeted reinnervation amputees, Brain, vol. 134, No. 3, p. 747, 2011.
Rohde, Di Luca et al., Public Library of Science (PLOS) ONE, vol. 6, No. 6, p. 21659, 2011.
Tsakiris et al., The Rubber Hand Illusion Revisited: Visuotactile Integration and Self-Attribution, Journal of Experimental Psychology: Human Perception and Performance, vol. 31, No. 1, p. 80, 2005.
Wilson et al. "Thermal Feedback Identification in a Mobile Environment," Proceedings of Haptic and Audio Interaction Design ("HAID"), 2013.

* cited by examiner

| Display type / View | Display with one cell | | Display with multiple cells (eight cells) | |
|---|---|---|---|---|
| | No Pressure | Pressure | No Pressure | Pressure |
| Side view | | | | |
| Top view | | | | |

Figure 6

MULTIMODAL HAPTIC DEVICE INCLUDING A THERMAL AND TACTILE DISPLAY UNIT, SYSTEM, AND METHOD OF USING THE SAME

CROSS-REFERENCE TO RELATED APPLICATIONS

The present application claims priority to the United States provisional application with the Ser. No. 62/117,476 filed on Feb. 18, 2015, the entire contents thereof are incorporated by reference.

TECHNICAL FIELD

The invention is in the field of haptics, more particularly of user interface devices for providing multimodal haptic feedbacks, as well as methods for using these user interface devices for haptic feedbacks.

BACKGROUND ART

The research in the field of human-machine interaction ("HMI") has been expanding in these last decades. Several modern breakthroughs such as tele-operated robotics, immersive virtual reality or augmented reality have pushed the limits and capacity of humans to interact with their environment a step further. Visual and auditory feedbacks are reaching such levels of realism that users can believe the environment they see and hear, be it remote or virtual, is physically tangible.

The growing variety of tasks that can be performed by controlling a teleoperated manipulator, such as robots or less automated devices, and their increasing importance call for more intuitive and reliable human-machine interfaces. Besides the evident advantage of allowing the user to control a manipulator from a remote location, teleoperation can also be used to enhance the user's perception by increasing the strength of a stimulus, be it visual or tactile, to filter the user's tremor, scale down/up his movements as well as the force applied, thus allowing for operation in restricted or unfriendly environments. Nowadays, teleoperated robots are used to inspect nuclear reactors, for rescue in catastrophic situations, for marine applications, or to perform minimally invasive surgeries ("MIS"), one of the most promising research directions where errors in the bidirectional communication with the user cannot be tolerated.

Also the use of robotic systems to perform complex surgical procedures is steadily increasing. While these robotic systems can improve performance, they currently provide visual feedback alone thus depriving the surgeon of important haptic information. Haptic feedback can be divided into force and tactile feedback, both essential for dexterous manipulation. Without force feedback the surgeon using a position-controlled teleoperated robot has a serious risk to damage internal tissues by applying too much force. In addition, some works have emphasized the benefits of introducing force feedback in robotic surgical systems in terms of usability and reduction of cognitive load. Our multimodal tactile perception allows us to discriminate the objects we manipulate based on their texture, compliance, shape and thermal characteristics by integrating these sensorial inputs in a congruent percept. By palpating the tissues, the surgeon can find hidden arteries based on pressure cues, for example the pulse, and discern cancerous tissues based on temperature alone. Interestingly, even in the absence of other relevant tactile cues, we are able to discriminate a variety of materials based on thermal cues alone. Another important factor for fine manipulation of a teleoperated system is its embodiment. Force feedback has been shown to increase embodiment of a virtual tool. Similarly, embodiment being a multisensory process, it is likely dependent on the congruency of the multimodal feedback as well.

Several haptic devices combine tactile and kinesthetic feedback, often by mounting a tactile display on a force feedback device. Recently, displays presenting several tactile modalities simultaneously to the user were designed. While current designs have reached satisfactory tactile stimulation, they are still limited due to their size and rigidity. Moreover, the haptic feedback, for example the combination of tactile and kinesthetic feedback, which is needed to truly make the environment tangible is of absent or considerably lacking realism compared to its visual and auditory counterparts. Most haptics actuators and devices can only display a limited amount of haptic cues. Typical actuators used in the field are vibrating eccentric motors or similar piezoelectric actuators providing warnings rather than realistic tactile cues. In addition, human tactile perception is multimodal; we need several cues, such as compliance, texture or temperature to identify objects. While multimodal tactile actuators exist, the technology is bulky, complicated and rigid. These limitations restrict their usage to specific predefined areas of the body and limiting their wearability and their integration with other devices such as the master of a teleoperated system.

Recently, a publication successfully used thermal feedback as a vector of information in environments in which audio or vibrotactile feedback might be masked by noise or movements. Wilson et al. "Thermal Feedback Identification in a Mobile Environment," Proceedings of Haptic and Audio Interaction Design ("HAID"), 2013. In their studies, thermal feedback is used instead of vibration to provide warnings about incoming cell phone messages. By varying thermal parameters such as subjective intensity, for example moderate warm, intensive cold etc., or direction of the temperature change, it was possible to inform the user on the urgency of the message. For example, very warm was used for urgent, mild warm was used for not urgent, or the identity of the sender, warm for family, cold for work for example. In addition, they found promising results for the identification of individual thermal parameters while sitting and walking outdoors. By combining thermal stimulation with multimodal tactile stimulation, a vast array of stimulations is available. These stimulations can provide rich encoded information to the user.

The importance of thermal cues in object, discrimination and their potential for telemanipulation has led to the development of various thermal displays. These devices are for the most composed of a Peltier element, a heatsink and a temperature sensor. One surface of the Peltier element is kept at a constant temperature by the heatsink while the other surface temperature is controlled using the sensor input in a feedback loop. These systems can be divided in two categories: in one the user's finger, or other body parts, is in constant contact with the display, in the other the contact between the user and the display happens only when a contact in the virtual or teleoperated environment occurs. A flexible and wearable device should therefore be in constant contact with the user.

The International patent publication No. WO 2009/061572 discloses a thermal haptic feedback system for generating thermal haptic effects. The system includes multiple cells, each of them providing heating or cooling in a generally isolated area that is approximately the size of the cell. Each cell can be independently controlled, allowing for the generation of complex thermal haptic patterns for generating haptic effects. In addition to thermal haptic effects, it is also described that each cell can include force feedback type haptic effects generated by, for example, actuators. Therefore, tactile cues are provided to the user with the use of further devices coupled to the thermal haptic system, thus rendering the system bulky and not completely compliant.

Despite some of the above-discussed advancements in the field of haptics, there is still an urgent need in the field for small, wearable, easily embeddable and multimodal tactile feedback devices.

SUMMARY

According to one aspect of the present invention, a device is provided that provides a haptic interface simulating both large scale haptics and small scale sensations for increased haptic fidelity. More specifically, preferably a haptic device is provided that is able to provide multimodal tactile feedbacks such as temperature, pulse, tapping pressure or variable compliance as well as force feedback in one single device. Disclosed herein are also methods of using such a device for several applications, including virtual/augmented reality, rehabilitation therapy and others.

According to another aspect of the present invention, the device is preferably flexible, wearable and adaptable to the user's anatomy, and can even, in one embodiment, provide thermo-tactile haptic feedbacks. Preferably, the device may include a portable actuation unit connected to a flexible display unit. A single actuation system can control the pressure and temperature of a fluid medium, such as liquid or a gas, to provide tactile, and possibly at the same time even temperature, cues, to the user touching the display. The tactile cues are created by controlling the shape of a flexible membrane of the display through the fluid medium pressure. Known multimodal displays contain several actuators, most of which rigid and requiring power and control cables for each actuator, thus making them hardly wearable, bulky and not user-friendly. Contrary to known tactile displays that make use of several rigid actuators in order to obtain a multimodal feedback, the device according to an aspect of the invention features one single actuation system that generates the integrity of the multiple haptic feedbacks, both tactile and proprioceptive.

Thermal cues can be provided by the heat exchange between the fluid medium and the user's skin through the same membrane. The temperature of the fluid medium stream flowing in the display is achieved by mixing several fluid streams at specific temperatures. These fluids are heated or cooled to specific temperatures, preferably by using Peltier elements, and can be stored in buffer tanks. The medium flow and pressure are controlled using a combination of micro pumps and valves. The flexible display is composed of an array of cells herein named tactile display cells. The number of cells and their disposition is modular in order to adapt the cell density to the type and surface of skin. The medium pressure and temperature can be controlled in each individual display cell using a system of valves and manifolds embeddable in the portable actuation unit. The tactile display can have different functional shapes adapted to the user's anatomy.

Accordingly, it is an object of the present invention to provide for a multimodal haptic device, preferably including at least one pipeline configured to allow a closed-loop flow of a fluid medium, at least one manifold operatively connected to said pipeline, including at least a pump and at least a valve to control and regulate the fluid medium's flow along the pipeline, and at least one display unit operatively connected to the pipeline, the display unit including a tactile display and at least a valve operatively connected to the display for regulating the efflux of the fluid medium from the display into the pipeline.

In preferred embodiment, the multimodal haptic device further includes at least one container comprising a fluid medium. In another preferred embodiment, the multimodal haptic device further includes at least a valve operatively connected to the display unit for regulating the influx of the fluid medium from the pipeline into the display. In a particular embodiment, the multimodal haptic device preferably includes at least two containers, each comprising a fluid at a specific temperature, two pipelines, each operatively connected by a manifold to at least one of the containers, and at least one display unit operatively connected to both pipelines.

In a preferred embodiment, the at least two containers are coupled by at least one Peltier element, and preferably the fluid medium is a liquid. In a more preferred embodiment, the fluid medium is water or a cooling aqueous solution. In a preferred embodiment, the display includes at least one inflatable chamber made of an elastic material, and preferably, the pipeline can be made of an elastic material.

In one embodiment, the multimodal haptic device includes one or more sensors for detecting and/or storing at least a user's physiological parameter, an environmental parameter or a combination thereof. In a preferred embodiment, the sensor is operatively connected to the display unit and/or the manifold. In another preferred embodiment, the sensor further includes a communication interface for wirelessly transmitting the detected and/or stored data concerning user's physiological parameter, an environmental parameter or a combination thereof to a computer or a mobile device. In a most preferred embodiment, the sensor further includes a communication interface for wirelessly receiving a feedback input from a computer or a mobile device able to regulate the functioning of the haptic device.

In one preferred embodiment, the multimodal haptic device is configured to be MM-compatible and/or waterproof, and in one embodiment, the multimodal haptic device is part of a garment, an exoskeleton, or it is incorporated within a garment or an exoskeleton.

In a preferred embodiment, the multimodal haptic device can provide different feedback information, for example pressure feedback, suction feedback, stretch feedback, texture feedback, humidity feedback, temperature feedback, pulse feedback, force feedback, vibration feedback or any combination thereof.

According to another aspect of the present invention, a method of using the multimodal haptic device is provided. Preferably, the method includes the steps of mounting a multimodal haptic device onto a user, the multimodal haptic device including a pipeline configured to allow a closed-loop flow of a fluid medium, a manifold operatively connected to the pipeline, the manifold having a pump and a valve to control and regulate a flow of the fluid medium along the pipeline, and a display unit operatively connected to the pipeline, the display unit having a tactile display and a valve operatively connected to the tactile display for regulating an efflux of the fluid medium from the tactile display into the pipeline, and operating the multimodal haptic device while mounted to the user, wherein the step of operating includes at least one of sport training, orthopaedics rehabilitation, remote surgery, embodiment in virtual reality settings, self-massage, self-relaxation, patient's mobilization, and counter conditioning for phobia treatment.

It is another object of the present invention to provide for methods of using the multimodal haptic device or system in different settings and conditions, such as for instance for sport training, limb immobilization or other orthopaedics applications such as orthopaedics rehabilitation, remote surgery, embodiment in virtual reality settings, self-massage, self-relaxation, patient's mobilization and/or counter conditioning for phobia treatment, among others.

The above and other objects, features and advantages of the present invention and the manner of realizing them will become more apparent, and the invention itself will best be understood from a study of the following description with reference to the attached drawings showing some preferred embodiments of the invention.

BRIEF DESCRIPTION OF SEVERAL VIEWS OF THE DRAWINGS

The accompanying drawings, which are incorporated herein and constitute part of this specification, illustrate the presently preferred embodiments of the invention, and together with the general description given above and the detailed description given below, serve to explain features of the invention.

Herein, identical reference numerals are used, where possible, to designate identical elements that are common to the figures. Also, the images are simplified for illustration purposes and may not be depicted to scale.

DESCRIPTION OF THE SEVERAL EMBODIMENTS

The present disclosure may be more readily understood by reference to the following detailed description presented in connection with the accompanying drawing figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

As used herein and in the appended claims, the singular forms "a," "and," and "the" include plural referents unless the context clearly dictates otherwise. Thus, for example, reference to "a display unit" includes a plurality of such display units and reference to "an actuation unit" includes reference to one or more actuation units, and so forth.

Also, the use of "or" means "and/or" unless stated otherwise. Similarly, "comprise," "comprises," "comprising" "include," "includes," and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of."

A "haptic device" is any device that exploits haptic technology. As used in the present disclosure, "haptic technology" or "haptics" is a feedback technology which recreates or stimulates the sense of touch by applying forces, pressures, temperatures, electrostimulations, vibrations and/or motions to the user. This mechanical stimulation can be used to assist in the creation of virtual objects in a computer simulation, to control such virtual objects, and to enhance the remote control of machines and devices (telerobotics). Haptic devices may incorporate sensors that measure forces, pressures or movements exerted by the user on the interface and vice versa. Haptic technology has made it possible to investigate how the human sense of touch works by allowing the creation of carefully controlled haptic virtual objects. These objects are used to systematically probe human haptic capabilities, which would otherwise be difficult to achieve. As research tools, moreover, haptic devices contribute to the understanding of how touch and its underlying brain functions work. A haptic device usually comprises a tactile display, a display device that presents information in tactile form (tactile feedbacks). The most common applications of the haptic technology include the provision of haptic feedbacks for controllers such as game controllers, joysticks, remote-controlled robotic tools, mobile devices such as mobile phones, virtual reality systems and so forth. Haptic interfaces for medical simulation may prove especially useful for e.g. training in minimally invasive procedures, as well as for performing remote surgery. In the context of the present disclosure, the haptic device of the invention is also interchangeably referred to as "the system".

The term "multimodal" refers herein to the characteristic way by which a haptic device according to the present disclosure provides a user with a feedback. In particular, a multimodal feedback allows a user to experience multiple modes of interfacing with the haptic device. Multimodal interaction is the interaction with a virtual and/or a physical environment through natural modes of communication. This interaction enables a freer and natural communication, interfacing users with automated systems in both input and output. However, in the frame of the present invention, the term multimodal refers more specifically to the several modes by which the haptic device can provide tactile feedbacks to a user. The human sense of touch can be divided into two separate channels. Kinaesthetic perception refers to the sensations of positions, velocities, forces and constraints that arise from the muscles and tendons. Force-feedback devices appeal to the kinaesthetic senses by presenting computer-controlled forces to create the illusion of contact with a rigid surface. The cutaneous class of sensations arise through direct contact with the skin surface. Cutaneous stimulation can be further separated into the sensations of pressure, stretch, vibration, and temperature. Tactile devices generally appeal to the cutaneous senses by skin indentation, vibration, stretch and/or electrical stimulation. The device of the present invention is construed and assembled in order to provide a tactile feedback involving one or more, possibly combined, among kinaesthetic or cutaneous sensations.

Multimodal devices can offer a flexible, efficient and usable system allowing users to interact through input modalities and to receive information by the device through output modalities. The multimodal device has to recognize the inputs from the different modalities, combining them according to temporal and contextual constraints in order to allow their interpretation, interpreting the fused inputs and returning to the user outputs arranged according to a consistent feedback.

A "closed-loop system", also known as a feedback control system, refers herein to a control system which uses the concept of an open loop system, in which the output has no influence or effect on the control action of the input signal, as its forward path but has one or more feedback loops or paths between its output and its input. The reference to "feedback" means that some portion of the output is returned back to the input to form part of the system's excitation. Closed-loop systems are usually designed to automatically achieve and maintain the desired output condition by comparing it with the actual condition. It does this by generating an "error" signal which is the difference between the output and the reference input. In other words, a closed-loop system is a fully automatic control system in which its control action is dependent on the output in some way.

A "manifold" refers herein to a system that regulates fluid flow between pumps and actuators and other components in a hydraulic or pneumatic system, with the aim of distributing the fluid throughout a circuit such as a pipeline. A manifold usually comprises pumps and also assorted valves operatively connected to each other. It is the various combinations of states of these valves that allow even complex control behaviour in a manifold.

As used herein, a "fluid" is a substance that continually deforms or flows under an applied shear stress. Fluids are a subset of the phases of matter and include liquids, gases, plasmas and plastic solids. They display properties such as not resisting deformation, or resisting it only lightly and the ability to flow, also described as the ability to take on the shape of the container.

In a preferred embodiment of the invention, the fluid comprises or consists of a liquid such as e.g. water, aqueous solutions, non-polar solutions for example but not limited to oil, and the like. An "aqueous solution" is a solution in which the solvent is substantially made of water. In the frame of the present disclosure, the term "aqueous" means pertaining to, related to, similar to, or dissolved in water. In the context of the present disclosure, the fluid according to the invention is also interchangeably referred to as "medium fluid" or simply "medium". A further suitable liquid to be used in accordance to the present disclosure can be a coolant aqueous solution such as for instance the TCS COOLANT™ supplied by TCS Micropumps™ Ltd. Such a liquid solution has further beneficial characteristics for the herein disclosed device as for example improvement of the contact at the interface between heat exchanger and coolant leading to increased thermal efficiency, inhibition or limitation of corrosion and/or algae and microbe growth, lubrication of pump seals, thus increasing pump life, reduction of air locks, and so forth.

In the context of the present disclosure, the expression "operatively connected" reflects a functional relationship between the several components of the haptic device among them, that is, the term means that the components are correlated in a way to perform a designated function. The "designated function" can change depending on the different components involved in the connection; for instance, the designated function of a manifold operatively connected to a container is the regulation of the fluid medium flow between the container and a pipeline via the opening/closing of valves and/or activation/deactivation of a pump. Similarly, the designated function of a valve operatively connected to a display is the regulation of influx/efflux of the fluid medium through said display.

A "display unit" is a portion of the device of the invention comprising a tactile display. A "tactile display" in the context of the present disclosure refers to an output device for presentation of information in a tactile form. A tactile display is a user-device interface that can reproduce as closely as possible the tactile parameters of an object, either real or virtual, such as shape, surface texture, roughness, temperature and so forth.

A "Peltier element" is a thermoelectric device that uses the Peltier effect to create a heat flux between the junction of two different types of materials. Also known as Peltier cooler, heater, or thermoelectric heat pump, it is a solid-state active heat pump which transfers heat from one side of the device to the other, with consumption of electrical energy, depending on the direction of the current. It can be used either for heating or for cooling, although in practice the main application is cooling. It can also be used as a temperature controller that either heats or cools.

An "elastic material" is a solid material having the tendency to return to its original shape after being compressed, stretched, expanded or otherwise deformed. An elastic material is particularly suitable for the manufacturing of the tactile display of the device of the invention, since it could permit, enhance or ameliorate the range of possible user's feedbacks provided by the display in terms of tactile sensations. A non-exhaustive and non-limiting list of suitable elastic materials according to the present invention comprises polymeric materials such as silicone, for example polydimethylsiloxane ("PDMS"), nitrile rubber, latex, polyurethane, polyisoprene such as synthetic rubber, any kind of elastomers, the Tango family of rubber-like materials, for example TangoPlus™ or FullCure930™ and the like.

The multimodal haptic device comprises one or more sensors for detecting and/or storing at least a user's physiological parameter, an environmental parameter or a combination thereof, which is operatively connected with at least one element of the haptic device. A "sensor" as used herein is a device that detects, and possibly responds to signals, stimuli or changes in quantitative and/or qualitative features of a given system, or the environment in general, and provides a corresponding output. The output is generally a signal that is converted to human-readable display at the sensor location or transmitted electronically over a network for reading or further processing. The specific input could be for instance light, heat, motion, moisture, pressure, or any one of a great number of other environmental phenomena. According to the present disclosure, a sensor preferably comprises a sensor device for detecting and/or storing user's physiological parameter, an environmental parameter or a combination thereof. The sensor can therefore comprise a data storage device to hold information, process information, or both. Common used data storage devices include memory cards, disk drives, ROM cartridges, volatile and non-volatile RAMs, optical discs, hard disk drives, flash memories and the like. The information detected and collected by said sensor can relate to a user's physiological parameter such as for instance muscle contraction, including postural muscle contraction, heart work rate, skin conductance, also called galvanic skin response ("GSR"), respiratory rate, respiratory volume, body temperature, blood pressure, blood level of organic/inorganic compounds, for example but not limited to glucose, electrolytes, amino acids, proteins, lipids, electroencephalogram, sweating and so forth. Alternatively or additionally, the information detected and collected by the sensor can relate to environmental parameters such as temperature, humidity, light, sounds, touch and the like. Preferably, the sensor further comprises a communication interface device for transmitting the detected and/or stored data concerning the above-mentioned parameters to a computer, and more preferably through a wireless connection. "Wireless" refers herein to the transfer of information signals between two or more devices that are not connected by an electrical conductor, that is, without using wires. Some communication interface devices of wirelessly transferring signals can be based on a variety of communication signals and standards, for example but not limited to WiFi, Bluetooth, magnetic, radio, telemetric, infrared, optical, ultrasonic connection, radio-frequency ("RF"), and the like.

In a most preferred embodiment, the sensor further comprises a communication interface device for wirelessly receiving a feedback input from a computer able to regulate the functioning of the device. In a preferred embodiment, the sensor is operatively connected to the display unit and/or the manifold. The main actuation unit controls all the cells in the device without any cable, depending on the configuration, but at least in the configuration where all the valves are on a main manifold. The main actuation unit could feature a printed circuit board ("PCB") with e.g. a microcontroller controlling all the components, for example but not limited to the pumps, the valves, the sensors and any other component mounted on the main manifold. For this reason, the board manages the low-level functions such as the closed feedback loop controlling the temperature and pressure in the cells. The board can be seen as a driver for the device communicating wirelessly with a computer or a mobile phone managing the high-level functions. For example, in an application in virtual reality, the computer simulates a virtual environment, when the user virtually touches an object in said environment, the properties of this object, stiffness, temperature, texture etc., are transmitted from the personal computer ("PC") to the microcontroller, in a wireless or cabled fashion, as simple commands such as: set temperature to this value, set stiffness to given value and the like.

Such an input feedback is particularly convenient when the device is supposed to be used for instructing the user on how and when to react to particular external inputs or even user's physiological parameters. For instance, the device can be used to teach a user to get into a specific posture, either e.g. in a rehabilitation or in a training setting. By collecting information by sensors on postural attitudes of the user, these can be sent and analysed by a computer that in turn can provide a tactile feedback to the user to instruct him/her on how to e.g. correct the erroneous posture position. This approach is particularly helpful for tracking and eventually correcting and/or fine tuning abnormal or incorrect postures in e.g. sport athletes, especially for those parts of the body that are not easily checkable by a trainer or the athlete him/herself such as but not limited to the trunk, shoulders, neck, feet, or even in conditions where monitoring is almost impossible, for example for swimmers performing in open waters.

To describe and illustrate more clearly the aspects of the present invention, the following examples are provided in detail, which however are not intended to be limiting of the invention. They show embodiments of the multimodal haptic device in accordance with some aspects of the invention.

As disclosed in the present exemplary embodiment, the device is a portable and light tactile display able to provide a multimodal tactile and force stimulation through a haptic interface simulating both large scale haptics and small scale sensations for increased haptic fidelity. According to another aspect, the device can be made wearable and adaptable to the user's anatomy.

The device is divided in two parts: an actuation unit 1, including a thermal conditioning unit 2a and a pressure regulation unit 2b, and the display 3. The thermo-tactile feedback is achieved by using the actuation unit 1 to control the temperature of one or several fluid medium streams. The pressure regulation unit 2b controls the pressure of the medium flowing through the display 3, for each unit, working as an interface with the user's skin.

The thermal conditioning unit 1 uses one or several Peltier element(s) 4 to contemporaneously heat the fluid medium, which could be liquid or gas, flowing on one surface while simultaneously cooling the medium flowing on its opposite surface. By doing so, the efficiency of the Peltier elements 4 is greatly increased compared to conventional applications when only one side of the Peltier elements 4 is used for thermal stimulation, while the other is forced to a constant temperature thus wasting power. Several Peltier elements 4 can be used in series to in turn cool down or warm up two fluid medium streams. In one embodiment, they can also be used in parallel thus creating several medium streams at different temperatures. The temperature of the fluid medium entering the display 3 is achieved by mixing streams of the medium at different temperatures. The temperature range of the device is set by the coldest and warmest stream.

Tanks 6 can be used to store the medium at different temperatures. These temperatures delimit the thermal working span of the device and are customizable. Tanks 6 work also as buffers compensating for the change in temperature resulting from the medium returning from the display 3.

The heat transfer between the Peltier element(s) 4 and the fluid medium is achieved through heat conduction and natural or forced convection. Furthermore, heat sinks 7, typically made of copper and aluminium, can be used to increase heat exchange. Accordingly, in one embodiment of the invention, the Peltier element(s) 4 can be interposed in between two tanks, thus heating and cooling the medium in both tanks through natural convection. In this configuration, the medium in the tanks can also be set into motion using a mixing system, thus achieving forced convection. In another embodiment, the Peltier element(s) 4 can be interposed in between two heat sinks and the medium pumped through the said heat sinks to achieve forced convection.

In one embodiment, the fluid medium is pumped through the heat sinks 7 and the heat transferred from the Peltier element(s) 4 is sufficient to rapidly reach the target medium temperature, both on the hot and cold side. In this configuration no tanks 6 are required, as instantaneous heating and cooling is provided.

The desired display 3 temperature is achieved by mixing various medium streams at different temperatures into a mixing chamber 8. However, in an alternative embodiment, this mixing can also take place directly inside the display 3. The temperature of the mixed fluid medium is regulated by controlling the proportions of hot and cold medium injected into the chamber of the display unit 3 using the pumps 9, the opening of the valves 10 or a combination of both. The temperature feedback is provided using temperature sensors in the display. Small sensors with low thermal inertia such as but not limited to thermocouples, thermistors, thermal resistances and the like are introduced inside the display through the pipelines.

The pressure regulation unit 2b can control the pressure in the display by using two components: the pump(s) to generate pressure and the valve(s), called outlet valves 10, placed at the outflow of the display(s) 3 to control the medium flow. By controlling the pressure applied by the pumps 9 and/or the valve 10 a precise control of the pressure in the display 3 is achieved. Pressure sensors can be placed after the inlet valves to provide pressure feedback at the display(s).

In a preferred embodiment, the entire system is sealed. By doing so, when a pump, for example the pump in the hot tank in a configuration with two tanks, takes medium out of a tank, the tank pressure drops. After the medium goes through the system and out of the display 3, it will be forced to return to the hot tank due to the pressure difference. If cold and hot medium is pumped from both tanks but in different proportions, for example a larger volume of hot medium than cold medium is pumped as the desired display temperature is rising, the mixed medium exiting the display will be divided between the two tanks according to the same proportions due to the different pressure drops in the two tanks. Thus, by sealing the system we ensure that both tanks remain full at all times, and in any position. In addition, by having the same proportions of medium returning to the corresponding tanks, the impact of the returning mixed medium on the tanks thermal equilibrium will be minimal, thus reducing the power consumption of the system.

Figure 1:
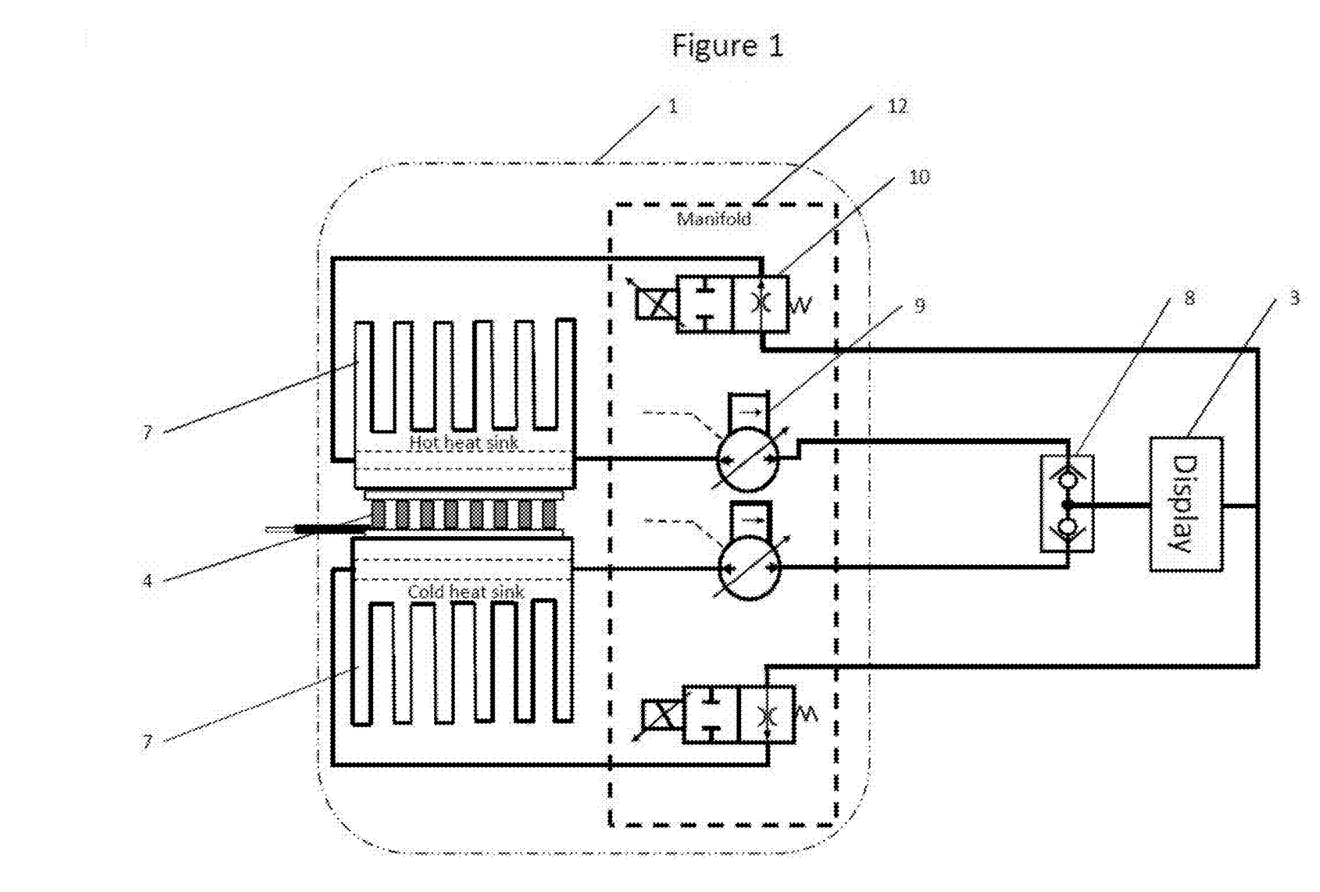
FIG. 1 shows a schematic representation of an embodiment of the device of the invention.

FIG. 1 shows a schematic representation of an embodiment of this system combining two previous embodiments. In this system, no tanks 6 are used and the medium goes through a hot and cold heat sink sandwiching a Peltier element. The power of the Peltier element is sufficient to bring the medium to the desired temperature almost instantaneously. The two medium streams are then mixed in the mixing chamber 8 connected to the display 3. The medium leaving the display consequently goes back to the appropriate tanks through two valves 10 mounted on the main manifold 12, itself mounted on the tanks 6, and that are used to control the pressure in the display 3.

In a preferred embodiment, a display 3 includes a main body 16 having one or several hollow chambers 17 located therein. This body can be made of rigid material, for example but not limited to plastic, metal, or of a flexible polymeric material such as PDMS. A thin elastic membrane 18 is attached on the main body 16, covering the hollow chamber(s) 17. The membrane 18 can be made out of any kind of polymer, such as a silicones or elastomeric materials. The material and thickness of the membrane 18 is selected based on the quantity of heat to be transferred and the desired elasticity, in order to obtain a convenient deformation of the membrane. The combination of a display hollow chamber 17 with the membrane 18 covering it is called a display cell 19.

Figure 2:
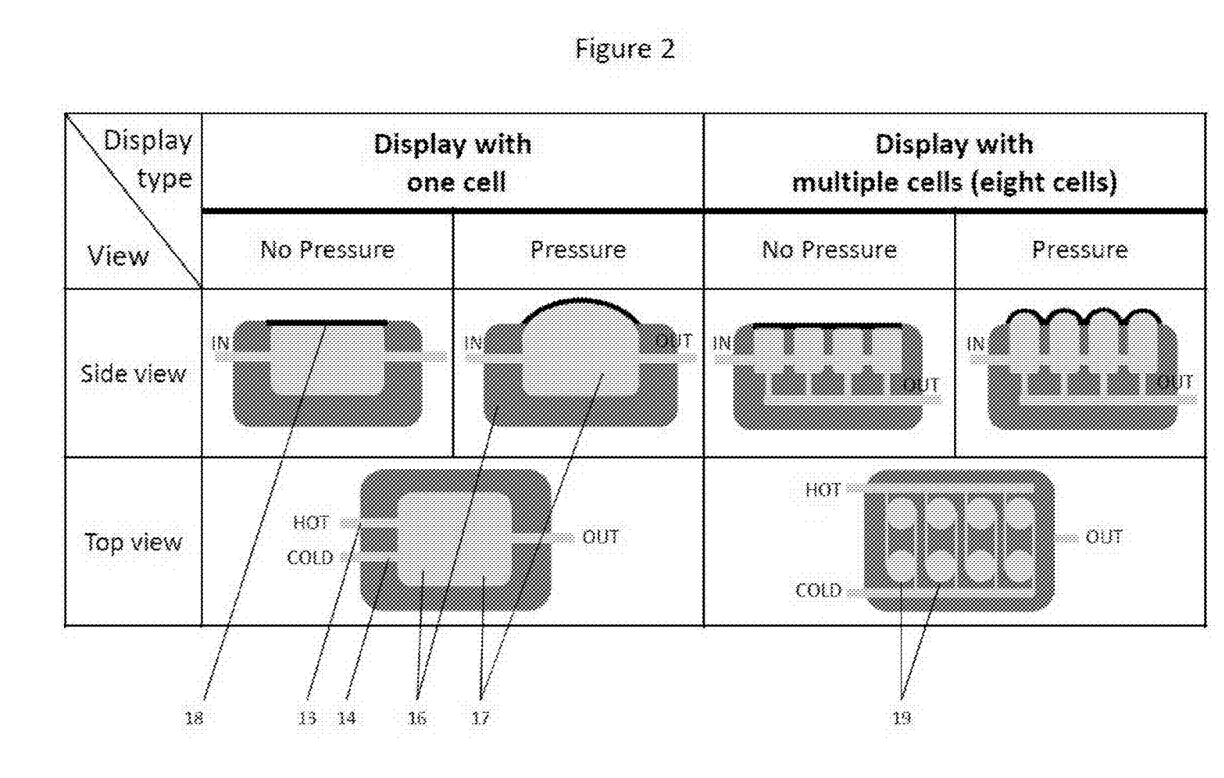
FIG. 2 presents a schematic sketch of two display types, one with a single display cell and another with multiple cells, in the pressured and resting states.

FIG. 2 presents a schematic sketch of two display types 3, one with a single display cell 19, the other with multiple cells 19, in the pressured and resting states. The display cells 19 size can vary depending on the tactile resolution of the skin stimulated, for example the hand, arm or torso, and the desired type of stimulus. When the fluid medium flows through the chamber, heat exchange will occur between the user's skin touching the membrane 18 and the medium. By building up the pressure inside the display cell, the membrane will inflate, thus providing a tactile feedback.

In a preferred embodiment, a display 3 includes a main body 16 comprising in it one or several hollow chambers 17. This body can be made of rigid material, for example rigid plastic, metal, etc., or of a flexible polymeric material such as Polydimethylsiloxane ("PDMS"). A thin elastic membrane 18 is attached on the main body 16, covering the hollow chamber(s) 17. The membrane 18 can be made out of any kind of polymer, such as a silicones or elastomeric materials. The material and thickness of the membrane 18 is selected based on the quantity of heat to be transferred and the desired elasticity, in order to obtain a convenient deformation of the membrane. The combination of a display hollow chamber 17 with the membrane 18 covering it is herein named display cell 19.

The size of the display cells 19 can vary depending on the tactile resolution of the skin stimulated, for example but not limited to hand, arm or torso, and the desired type of stimulus. When the fluid medium flows through the chamber, heat exchange will occur between the user's skin touching the membrane 18 and the medium. By building up the pressure inside the display cell, the membrane will inflate, thus providing a tactile feedback.

Figure 3:
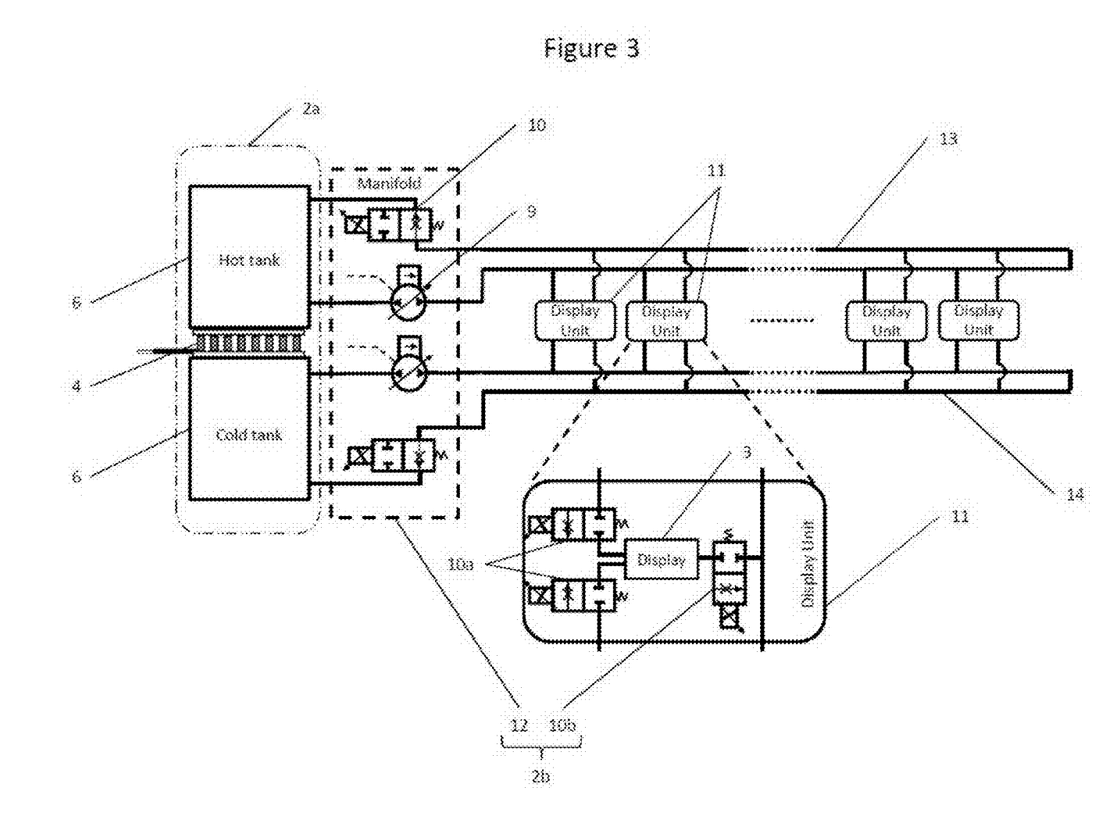
FIG. 3 shows a schematic view of another embodiment of the system.

FIG. 3 shows a schematic view of one embodiment of the system. It features two tanks, one comprising a cold fluid medium and one comprising a hot fluid medium, with a Peltier element interlaid between both tanks. The main manifold 12 includes two pumps 9 and two valves are mounted on the tanks 6. The two pumps 9 move the medium from the hot and cold tank into two pipes respectively leaving the manifold. These two pipes, named the hot main line 13 and cold main line 14, bring the hot and cold medium close to the area(s) that need(s) to be stimulated. The mediums from the hot and cold line than flow back to the hot and cold tanks 6 through the manifold valves. These flows in and out of the tanks 6 generate movement of the medium in the tanks and thus forced heat convection between the Peltier element 4 and the medium 5, thus increasing the efficiency of the system. By storing hot and cold medium 5 in tanks 6 and mixing them to obtain the desired temperature at the display 3, extremely high rates of temperature change can be achieved.

Display units can be attached at different locations along the cold and hot lines. A display unit 11 consists in a display 3 and three valves 10, for example a solenoid or proportional. The display unit 11 unit has two inputs, from the hot and cold line respectively. Two inlet valves 10a are used to control the amount of the hot and cold medium entering the display. The mixing of the two medium takes place directly in the display. Finally, the outlet valve 10b is used to control the pressure inside the chamber as previously explained. When the temperature and the pressure in the display cell correspond to the desired level, both the inlet and outlet valves are closed, thus isolating the display unit from the hot and cold main lines.

The cell resolution of this display is scalable to any size and density. Also, the same actuation unit will control any shape of display, and the display shape can be adapted to the function.

The number of display units and their size does not influence significantly the performance of the device nor its autonomy. More precisely, when the thermal feedback, obtained by mixing different mediums, is given on more displays, additional thermal perturbation is added in the tanks and more valves are involved. However, the thermal perturbations are well absorbed by the thermal inertia of the tanks, and the Peltier element work is not affected. Similarly, the system can generate tactile feedback on multiple displays by only modifying the valves activation and not the pumps activation. Since the valve consumption is extremely small compared to other components including the pumps and the Peltier element, adding additional displays does not affect the autonomy significantly. Since the actuation is centralized, it is easy to add valves for additional displays on the manifold.

Figure 4:
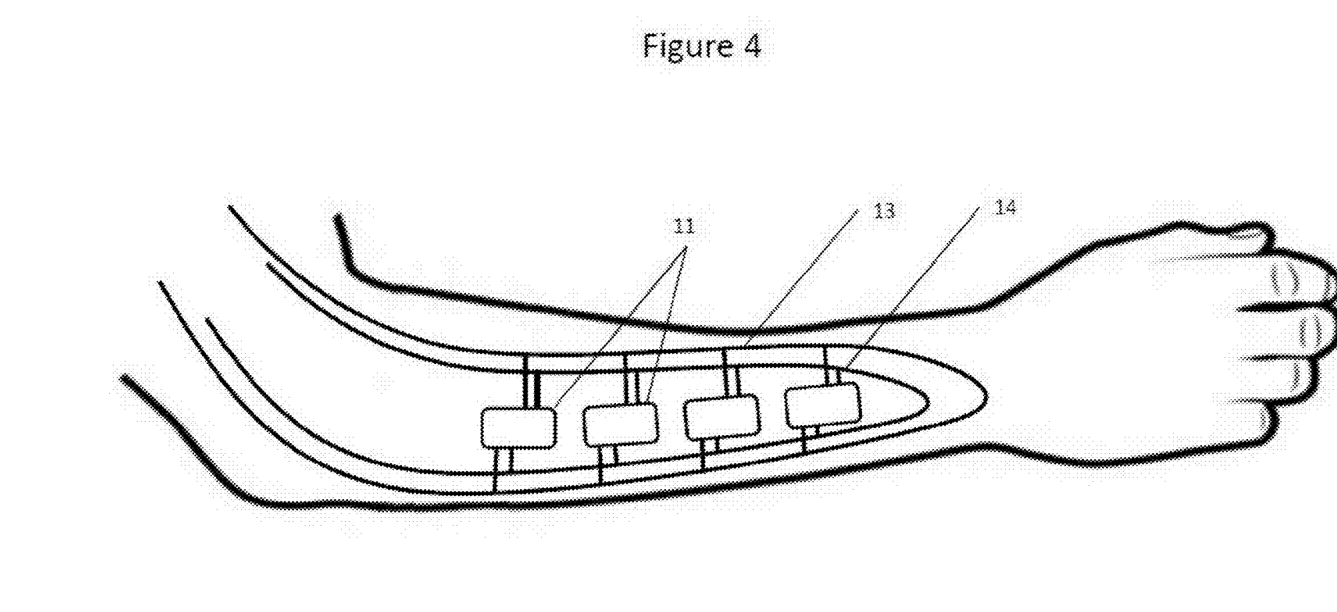
FIG. 4 shows an embodiment of the present device where four displays units are worn on the forearm.

FIG. 4 shows an embodiment of the present device where four displays units are worn on the forearm.

Figure 5:
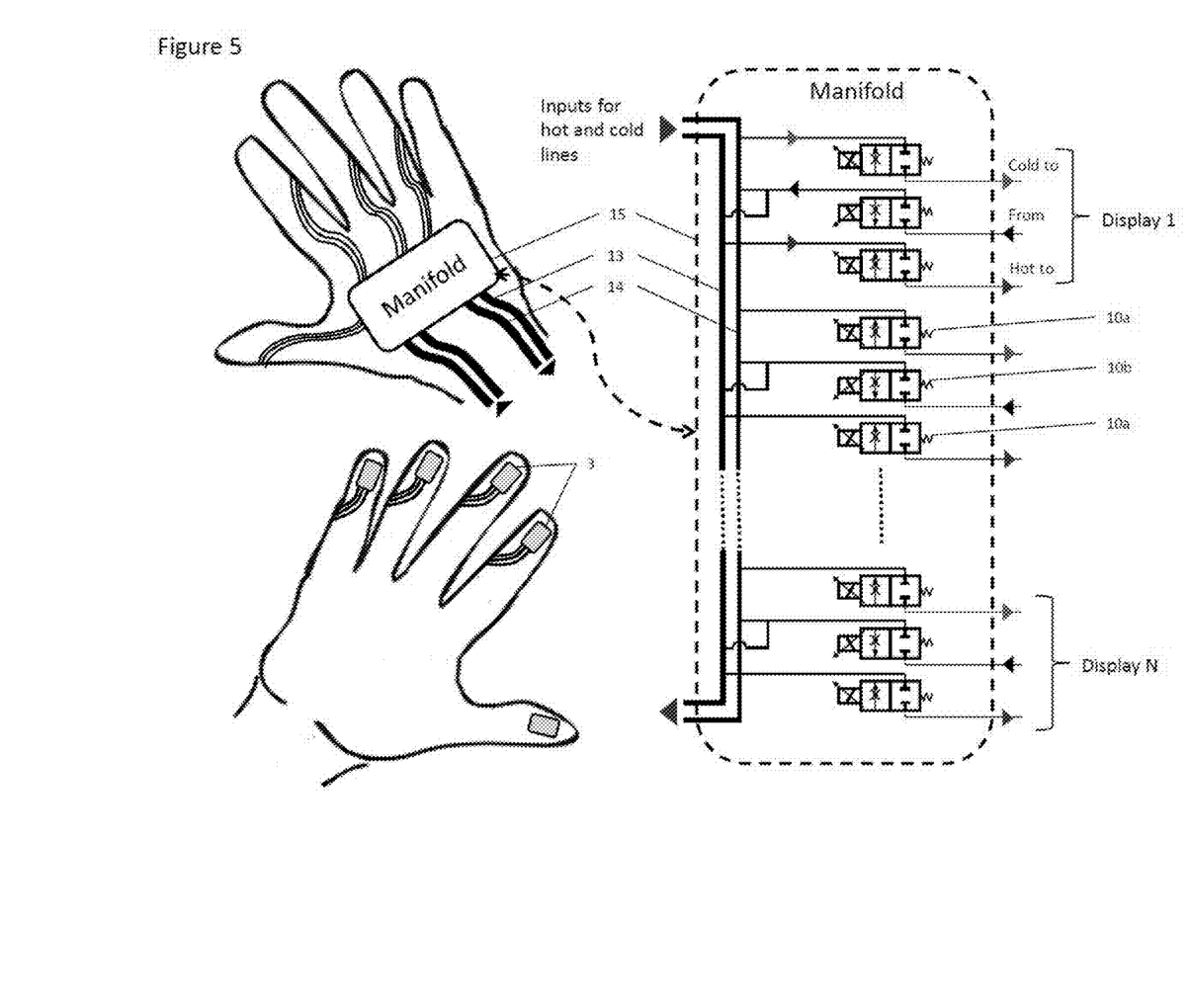
FIG. 5 shows another embodiment of the previous layout.

FIG. 5 shows another embodiment of the previous layout. In this case a display cell is worn on each finger. Since in this configuration the area to be stimulated is small, the inlet 10a and outlet valves 10b regulating the pressure and flow in each display cells cannot be placed directly on the finger and are located remotely on a manifold 15 worn on the back of the hand. This manifold is connected to the hot and cold main lines. It has three connections, 2 outlets for the hot and cold medium and 1 inlet for the mixed return medium, and three valves for each display. The number of displays 3 varies depending on the number of fingers to be stimulated, and number of cells per finger.

In another embodiment of this device all the valves from the displays, for example three (3) valves per display, are placed on the main manifold 12 over the tanks 6. By doing so there are only pipes going out of the main control/actuation unit and no valves or other manifolds have to be placed elsewhere along the device. On the other hand, there will be three pipes connected to each display. This solution is ideal when a smaller number of display is required as it reduces the system complexity.

The placement of the valves 10 is flexible and can be changed depending on the application. In another embodiment of the device, the inlet valves 10a are placed next to their display 3, but the outlet valve 10b is placed in the main manifold over the tanks. This is a hybrid embodiment combining two previous designs. Thus, depending on the application and the complexity of the stimulation to be performed, the system can be centralized in one main actuation unit or decentralized over several light manifold placed at the area(s) of interest.

In another embodiment of the device four pumps are used instead of two. There are two pumps per tank, one is placed upstream, the other downstream. The pump downstream must be a self-priming pump. By doing so, a precise control of the pressure in the display during medium flow is achieved. In fact, with only one pump pushing, the pressure in the display during the flowing phase is dependent on the hydraulic load following the display while with one pump pushing and the other sucking the pressure in the display during the flowing phase is controllable.

Figure 6:
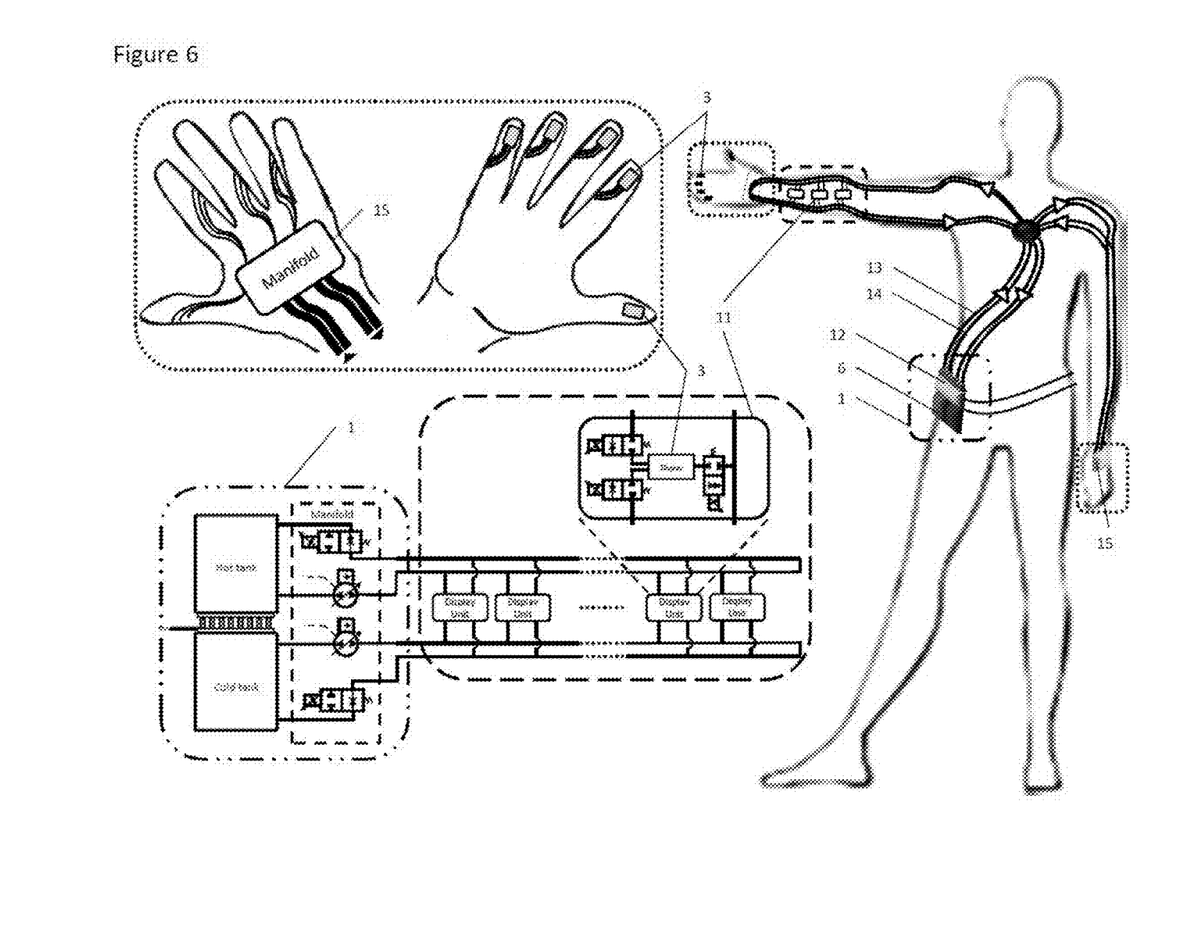
FIG. 6 illustrates an example of how the device is worn.

FIG. 6 illustrates an example of how the device is worn. The user can wear the main unit around the waist with a belt. The hot and cold lines come out of the manifold and are each spitted in two at the level of the chest. Several display units with their corresponding three (3) valves are placed on the forearm, and there is also a display on each finger with the valves mounted all together on the manifold attached on the hand.

In one embodiment of the present invention, the display cells, the sensors, the valves, the pumps and the piping are combined into one flexible polymer skin. This is done by molding polymers such as PDMS or by three-dimensional ("3D") printing the display using rapid prototyping machines with flexible materials, for example by the use of Tango Black Plus™. Using these production methods, the display can be fabricated with functional shapes such as garments like a sleeve, a glove, a ring-shaped display and so forth. Printed electronics using functional inks could be used to integrate the sensing directly in the membrane of the cells. For the temperature sensing, a thermocouple is created by printing two lines of different semiconductors that overlay each other in one point. This thermocouple is ideally placed because it is in contact with the skin. It is flexible and does not get damaged by bending the device and other mechanic constraints. Finally, in addition to the sensors, the wires going from the control/actuation unit to the display(s) can be printed, thus removing free wires from the system. Deformation sensors can be produced by printing strain gauges on the edges of the display membrane. Moreover, the valves and/or the pumps can even be microvalves and micropumps, and can be molded or printed as part of this skin. Those elements can be substantially made of an elastic polymeric material, possibly manufactured through microfluidic manufacturing techniques, e.g. photolithography, polymers molding techniques and the like.

In a further scenario, the actuation unit and piping system of the haptic device of another embodiment of the present invention uses an exoskeleton providing mobilization of the user's limbs or entire body. In the case of a full body exoskeleton, the system can provide verticalization, force feedback, postural stability and/or mobilization of the user, thus providing active walk assistance. The herein disclosed actuation unit is used as a pneumatic/hydraulic transmission actuating an articulated mechanical structure attached to a given body part. Furthermore, in a preferred embodiment, by applying high enough pressure it would be possible to rigidify the piping structure and successfully sustain and stabilize the user thereby replacing the mechanical structure. Then, by varying the pressure in the pipeline, forces are applied on specific limbs in order to mobilize them. Importantly, this exoskeleton is able to contemporaneously mobilize the user and providing all the haptic feedback modalities already described herein, thus making it a unique multimodal exoskeleton. These features make this exoskeleton an ideal tool for rehabilitation as it provides contemporaneous motor and sensory feedback in combination with the limbs mobilization which was found to be beneficial for cognitive aging and stroke patients as well as in many neurological pathologies resulting in a loss of somatic sensation. See L. A. Connell, Sensory Impairment and recovery After Stroke, PhD thesis, University of Nottingham, 2007. Stimulating these patients using various tactile stimuli, including temperature, can reactivate and rebuild neuronal pathways. See G. Nelles, Restorative Neurology and Neuroscience, Vol. 22, pp. 239-244, 2004. Therefore, the combination of sensorial neuro-rehabilitation, mobilization and force feedback is a promising solution for present and future rehabilitation therapies. Another key advantage of this exoskeleton is its inherent transparency. The transparency describes the amount of perturbation that a passive, non-activated, exoskeleton applies on the user. The more an exoskeleton is transparent, the less it will hinder the movements of the user when it is worn passively. A limb or full-body exoskeleton comprising the multimodal haptic device of the invention would be completely transparent when no pressure is applied in the pipes. Advantageously, it could also be used by healthy subjects to improve human performances and assist in specific tasks. For example, it can help the user lifting heavy weights by building up pressure in the pipes along the legs and later release the pressure to allow the user walk freely, as if the device was not there. Finally, the exoskeleton can be partial and only be worn and assist specific body areas, for example an arm exoskeleton with multimodal haptic feedback for stroke patients.

With the features of the present haptic system, multiple tactile feedbacks are provided, as well as force feedback that can be displayed individually or simultaneously:

(1) The pressure control system is used to control the stiffness of the display membrane. By building up pressure, the display becomes stiffer and vice versa. A dynamic control of the pressure can be also provided, in order to create a pulse feedback similar to e.g. the pulsation of an artery. This is done by building up the pressure in the chamber, thus inflating the membrane, and subsequently releasing the pressure.

(2) In an additional or alternative embodiment of the invention, by driving the pumps in the opposite direction while keeping the outlet valves 10b closed, suction at the level of the display membrane is generated, thus providing suction feedback.

(3) In an additional or alternative embodiment of the invention, by using a main body 16 with lower rigidity, it is possible to combine the orthogonal deformation of the membrane with a tangential deformation of the main body. This will provide an additional tactile feedback, i.e. a lateral skin stretch.

(4) In an additional or alternative embodiment of the invention, the membrane has a high porosity. This in turn increases the humidity under the user's skin. By applying pressure, or suction, it is possible to control the humidity, thus providing humidity feedback.

(5) In an additional or alternative embodiment of the invention, the display has a high density of small tactile cells used to generate a texture under the user's skin. In a passive version, the user's skin is moving on the display and the user can feel the edges due to the inflated cells. In the active version, the user's skin is immobile on the display and the cells are activated in specific spatiotemporal patterns giving the illusion of stroking a specific texture.

(6) In an additional or alternative embodiment of the invention, force feedback can be achieved at any point of the device by e.g. building up the pressure in the lines instead that in the displays. By closing all the inlet and outlet valves of the displays and the outlet valves 10b in the main manifold, the pumps will build up pressure in the pipes, rigidifying them. Relief and bypass valves can be used to keep a specific area of the pipe line under pressure while releasing pressure from the rest of the line, thus focusing the force feedback on that specific area.

(7) In an additional or alternative embodiment of the invention, the inlet valves 10a are solenoid valves driven with an adjustable pulse width modulation ("PWM") frequency. The fast switching of the valve generates a vibration that moves along the pipe. If the display 3 is placed in vicinity of the valve, this vibration is transmitted to the membrane, thus creating vibration feedback under the skin. This fast switching frequency can be in the range of 220 Hz, the frequency at which the skin mechanoreceptors ("FA") have the strongest response. When the vibration feedback is not required, the inlet valves can simply be used as ON/OFF valves. The control of the temperature in the display with the valves 10 does not require high frequency shifting, for example the hot medium inlet valve can stay open until the display medium heats up to the desired temperature and be closed afterwards.

(8) In an additional or alternative embodiment of the invention, a pinching force feedback is generated between two fingers by connecting a third display cell to the cells on each finger. This new middle cell, herewith named stiffness cell, can have the same design as previously described cells, with a main body and a membrane. Alternatively, it can have a main body with two membranes, one on top of the main body and the other on its bottom. It can also have only two membranes attached to each other, thus making a balloon. This chamber can be filled with the fluid medium and its stiffness, similarly to the stiffness feedback applied on the individual fingertips, can be changed by modifying the pressure of the medium inside the chamber. The stiffness of the cell, as well as the flexibility of its membranes, depends on the displacement required for the pinching movement and the forces required.

The device or system according to the aspects of the present invention can be used for several different applications. For example, it is possible to provide a self-massage, self-relaxation and counter conditioning for phobia treatment device, system, or method. In this respect, the multimodal haptic device can be used in combination with sensors that can track the user's body position and movement, for example an accelerometer or gyroscope, as well as physiological parameters, for example body temperature and skin conductance. In a specific embodiment of the invention, when combined movement sensors, the haptic feedback administered by the haptic device can be directly controlled by the user. Thus, movements of e.g. the user's hands can be translated into a specific pattern of haptic stimulation on the user's body. This will provide the user with the possibility to easily and comfortably perform actions such as self-massage in any part of his/her body or, similarly, it can be used as a tool to enhance relaxation techniques such as progressive muscle relaxation in an automatize and always-available fashion. As the multimodal haptic device can be embedded in a garment, the self-massage or treatment can be administered during real-life situations, for example when the user is walking in the streets, and not only in a controlled environment such as home or gym settings.

Self-relaxation techniques are widely used in behaviour therapy and counterconditioning techniques for the treatment of phobias, stress or anxiety disorders. The multimodal haptic device of the invention can be used as a tool to enhance this type of therapies, for example but not limited to systematic desensitization, flooding, immersive therapy etc. In a typical systematic desensitization therapy, for example to therapy snake phobias, the therapist follows a procedure comprising these three steps:

(1.1) Establishing anxiety stimulus hierarchy. A therapist may begin by asking the patient to identify a fear hierarchy. This fear hierarchy would list the relative unpleasantness of various levels of exposure to a snake. For example, seeing a picture of a snake might elicit a low fear rating, compared to live snakes crawling on the individual—the latter scenario becoming highest on the fear hierarchy.

(1.2) Learning coping mechanisms or incompatible responses. The therapist would work with the patient to learn appropriate coping and relaxation techniques such as meditation and deep muscle relaxation responses.

(1.3) Connecting the stimulus to the incompatible response or coping method. The patient would be presented with increasingly unpleasant levels of the feared stimuli, from lowest to highest—while utilizing the deep relaxation techniques, for example by progressive muscle relaxation, previously learned. The imagined stimuli to help with a phobia of snakes may include: a picture of a snake; a small snake in a nearby room; a snake in full view; touching of the snake, etc. At each step in the imagined progression, the patient is desensitized to the phobia through exposure to the stimulus while in a state of relaxation. As the fear hierarchy is unlearned, anxiety gradually becomes extinguished.

In this scenario, the multimodal haptic device could be used to enhance the relaxation techniques described in steps (1.2) and (1.3) mentioned above, therefore possibly boosting the effect of the therapy.

Previous technological scenarios in the field involved the use of immersive virtual reality system that allows to perform the behaviour therapy in a highly realistic and controlled environment, see e.g. U.S. Pat. No. 6,425,764.

Crucially, a wearable version of the multimodal haptic device not only allows to use the conditioned stimuli, for example pleasant and relaxing haptic feedback coupled during the therapy with the stimulus producing a certain phobia, unconditioned stimulus, during the therapy, but also during real-life situations, possibly reinforcing the well-known positive effects of counterconditioning for phobias and anxiety disorders. Thus, in the example of the snake phobias, the relaxing self-administered multimodal haptic stimulations used as conditioned stimuli during the therapy could be presented to calm down the patient when seeing real snakes in a real-life situation, for example in a zoo. In these situations, the multimodal haptic feedback could be actioned either by the subject himself or automatically through the monitoring of physiological parameters that are known to reflect several states of arousal, for example the measurement of skin conductance or body temperature. The multimodal haptic device will therefore not only be used as an aid in behaviour therapy but also as a "prosthetic" device, supporting the patients during real-life conditions when phobias or anxiety disorders are actually experienced. Several sensors combined with the multimodal haptic device could be used to record the user's physiological states during such real-life expositions to the phobias and inform the therapist about the efficacy of the treatment.

In the last decade, research in cognitive neuroscience has proposed multisensory integration to account for the underlying mechanisms of bodily self-consciousness—the non-conceptual and pre-reflective representation of body-related information. See e.g. Blanke, Nature Reviews Neuroscience, Vol. 13, No. 8, pp. 556-571, 2012. It has been shown that the sense of ownership, or self-identification, for one's own body parts, for example the feeling that this is my limb, and the location of these body parts, such as self-location, can be experimentally manipulated. For example, in the so-called rubber hand illusion ("RHI") synchronous stroking of one's, hidden, real hand and a seen fake hand, causes the fake hand to be misattributed to one's body. See Botvinick et al., Rubber hands 'feel' touch that eye see, Nature, Vol. 391, No. 6669, pp. 756-756, 1998, see e.g. Ehrsson et al., That's My Hand! Activity in Premotor Cortex Reflects Feeling of Ownership of a Limb Science, Vol. 305, No. 5685, pp. 875-877, 2004, see e.g. Tsakiris et al., The Rubber Hand Illusion Revisited: Visuotactile Integration and Self-Attribution, Journal of Experimental Psychology: Human Perception and Performance, Vol. 31, No. 1, p. 80, 2005. Under such multisensory conflicts, vision typically dominates over proprioception and touch. Indeed, several studies have shown that the rubber hand illusion also induces a mislocalization of one's hand towards the fake hand. See Rohde, Di Luca et al., Public Library of Science (PLOS) ONE, Vol. 6, No. 6, p. 21659, 2011. This is called "proprioceptive drift" and refers to the fact that, during synchronous stroking of the fake and the real hand, one's own hand is incorrectly localized as being closer to or shifted towards the rubber hand. See Armel et al., Projecting Sensations to External Objects—Evidence from Skin Conductance Response, Proceedings of the Royal Society of London. Series B: Biological Sciences, Vol. 270, pp. 1499-1506, 2003, see e.g. Austen, Soto-Faraco et al., Cognitive, Affective, & Behavioral Neuroscience, Vol. 4, No. 2, pp. 170-181, 2004, Tsakiris and Haggard 2005 mentioned supra. The global aspects of bodily self-consciousness, notably global ownership, or self-identification with a whole body, and self-location, have been also experimentally manipulated through the combined use of virtual reality and multisensory conflict situations, see Ehrsson, The Experimental Induction of Out-Of-Body Experiences, Science, Vol. 317, No. 5841, p. 1048, 2007, see e.g. Lenggenhager et al., Video Ergo Sum—Manipulating Bodily Self-Consciousness, Science, Vol. 317, No. 5841, p. 1096, 2007. Thus, viewing a virtual replacement of one's own body from a distance and form a third person prospective, via a camera and head-mounted display, being touched while synchronously feeling the touch on one's own body causes both the experience of feeling the virtual body as one's own body and the mislocalization of oneself outside one's own body and towards the virtual, like an illusory extracorporeal self-location.

The multimodal haptic device of the invention could be used in combination with other augmented-reality or immersion devices, e.g. audio or video devices, to induce systematic changes in bodily self-consciousness during real-life situations, for example when the user is walking in the street, and not only in a controlled environment, for example at home or gym settings. Positive effects of bodily manipulations have already been reported for treating pain. Hansen, Lenggenhager et al., Seeing and identifying with a virtual body decreases pain perception, European journal of pain, Vol. 15, No. 8, pp. 874-879, 2011. Also, the restoring bodily sensations in de-afferented patients with tetra- and paraplegia or amputation has been confirmed. Marasco, Kim et al., Robotic touch shifts perception of embodiment to a prosthesis in targeted reinnervation amputees, Brain, A Journal of Neurology, Vol. 134, No. 3, p. 747, 2011. The multimodal haptic device could possibly enhance these effects by making bodily manipulations portable and thereby always available. Similarly, the multimodal haptic device could be used to manipulate bodily self-consciousness to enhance gaming experience allowing to "feel" a digital body as one's own.

Another application for the system, device, and method of the present invention is the use for Limb immobilization and orthopaedics rehabilitation. Limb immobilization and non-use are well-known causes of both functional and cortical changes in limb kinematics. See Bassolino et al., Functional Effect of Short-Term Immobilization, Kinematic Changes and Recovery on Reaching-to-Graps, Neuroscience, Vol. 215, pp. 127-134, 2012, see e.g. Avanzino et al., Use-Dependent Hemispheric Balance, Journal of Neuroscience, Vol. 31, No. 9, pp. 3423-3428, 2011. Recently, it has been demonstrated that the maintenance of dynamic proprioceptive inputs in an immobilized arm through muscle vibration can prevent the hemispheric unbalance induced by short-term limb disuse. Avanzino et al., Shaping Motor Cortex Plasticity Through Proprioception, Cereb Cortex, Vol. 24, pp. 2807-2814, 2013. Sensory stimulation, especially, but not exclusively proprioceptive stimulation, by employing a version of the multimodal haptic device could be used to regain awareness over the affected body part, for example a body part suffering immobilization due to a cast or non-use due to peripheral or central damage, thereby possibly reducing corticomotor depression and fostering recovery in orthopaedics or neurological patients, e.g. stroke, spinal cord injury etc.

Yet another application for the system, device, and method of the present invention is the use for haptic communication and memory. The multimodal haptic device of the invention, combined with different type of haptic sensors, might also be used to record and subsequently re-experience haptic events, as it now already possible for vision and audition, through cameras and projectors or microphones and loud speakers. It could be used to enhance social communication or interaction and share haptic experience between different users in any real-life setting, i.e. home, walking in the street, sitting in a train etc.

Still another application for the system, device, and method of use for the present invention is to extent sensory capabilities to establish super-capacities. The multimodal haptic device could be further used to create artificial modalities that would allow to both map extended sensory capabilities, e.g. the output of an infrared sensor into a specific pattern of somatosensory stimulations, and properly integrate them with existing sensory modalities, during real-life conditions. See Dadarlat et al., A learning-based approach to artificial sensory feedback leads to optimal integration, Nature Neuroscience, Vol. 18, No. 1, pp. 138-144, 2015. This solution for providing super-capacities through haptic feedback represents a relevant advancement with respect to similar possible techniques using augmented reality through other modalities, for example vision and audition. Indeed, differently from vision and audition that are constantly implied in real-life tasks, haptic interactions are typically restricted to hand-object manipulations leaving a large part of our skin, particularly the trunk, excluded from our interaction with the surrounding environments. Thus, haptic stimulations in such regions of the body could be used to provide on-line feedback during real-life situations, while reducing the risk to overload the user's mind.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

The invention claimed is:

1. A multimodal haptic device comprising:
a first pipeline for circulating a first fluid, the first pipeline operatively connected to a first pump for controlling at least one of a pressure and a flow of the first fluid, the first fluid having a first temperature;
a second pipeline for circulating a second fluid, the second pipeline operatively connected to a second pump for controlling at least one of a pressure and a flow of the second fluid, the second fluid having a second temperature; and
a display unit operatively connected to the first and second pipeline and a valve, the display unit having a tactile display, the valve regulating flows of the first fluid and the second fluid between the tactile display and the first and second pipeline, to control both a temperature of the tactile display by mixing the first and second fluids, and a pressure exerted by the tactile display,
wherein the first and second pipelines and the display unit are arranged to form a closed-loop fluid system.

2. The multimodal haptic device of claim 1, further comprising:
a first container including the first fluid operatively connected to the first pipeline; and
a second container including the second fluid operatively connected to the second pipeline.

3. The multimodal haptic device of claim 2, wherein the first container and the second container are coupled together with a Peltier element.

4. The multimodal haptic device of claim 1, wherein the first and second fluid are liquids.

5. The multimodal haptic device of claim 4, wherein the liquids are at least one of a water and a cooling aqueous solution.

6. The multimodal haptic device of claim 1, wherein the tactile display includes an inflatable chamber made of an elastic material.

7. The multimodal haptic device of claim 1, wherein the pipeline is made of an elastic material.

8. The multimodal haptic device of claim 1, further comprising:
a sensor for detecting at least one of a physiological parameter of a user, and an environmental parameter.

9. The multimodal haptic device of claim 8, wherein the sensor is operatively connected to the display unit.

10. The multimodal haptic device of claim 8, wherein the sensor further includes a communication device for wirelessly transmitting at least one of the detected physiological parameter of the user and the environmental parameter to a data processing device.

11. The multimodal haptic device of claim 8, wherein the sensor further includes a communication device for wirelessly receiving a feedback input from a processing device to enable a control of the multimodal haptic device.

12. A wearable device including the multimodal haptic device of claim 1.

13. An MRI-compatible device including the multimodal haptic device of claim 1.

14. The multimodal haptic device of claim 1, further comprising:
at least one of a garment and an exoskeleton,
wherein the first and second pipelines and the display unit are incorporated within the at least one of the garment and the exoskeleton.

15. The multimodal haptic device of claim 1, wherein the display unit is configured to provide at least one of pressure feedback, tapping feedback, suction feedback, stretch feedback, texture feedback, humidity feedback, temperature feedback, pulse feedback, force feedback, and vibration feedback.

16. A method comprising the steps of:
mounting a multimodal haptic device according to claim 1 onto a user; and
operating the multimodal haptic device while mounted to the user,
wherein the step of operating includes at least one of sport training, orthopaedics rehabilitation, remote surgery, embodiment in virtual reality settings, self-massage, self-relaxation, patient's mobilization, and counter conditioning for phobia treatment.

17. The multimodal haptic device of claim 2, further comprising:
a sensor for detecting at least one of a physiological parameter of a user, a motion of a user, and an environmental parameter,
wherein the sensor is operatively connected to at least one of the display unit, the first pump, and the second pump.

18. The multimodal haptic device of claim 2, wherein the display unit further includes an additional valve and a manifold arranged to be in fluid communication with the first and second pipeline.

19. The multimodal haptic device of claim 1, wherein the first pipeline and the second pipeline are coupled together with a Peltier element.

20. The multimodal haptic device of claim 1, wherein the second temperature is different from the first temperature.

21. The multimodal haptic device of claim 2, wherein the display unit further includes a first valve operatively connected between the first pipeline and the display unit, and a second valve operatively connected between the second pipeline and the display unit.

* * * * *